(12) United States Patent
Mansfield et al.

(10) Patent No.: US 6,533,912 B2
(45) Date of Patent: *Mar. 18, 2003

(54) INCREASED THROUGHPUT ANALYSIS OF SMALL COMPOUNDS USING MULTIPLE TEMPORALLY SPACED INJECTIONS

(75) Inventors: Elaine S. Mansfield, Sunnyvale, CA (US); Christine Peponnet, Tiguery (FR); John S. Bashkin, Fremont, CA (US); Curtis R. Kautzer, San Jose, CA (US)

(73) Assignee: Molecular Dynamics, Inc., Sunnyvale, CA (US)

(*) Notice: Subject to any disclaimer, the term of this patent is extended or adjusted under 35 U.S.C. 154(b) by 29 days.

This patent is subject to a terminal disclaimer.

(21) Appl. No.: 09/859,840

(22) Filed: May 16, 2001

(65) Prior Publication Data

US 2001/0053554 A1 Dec. 20, 2001

Related U.S. Application Data

(63) Continuation of application No. 09/712,013, filed on Nov. 13, 2000, now abandoned, which is a continuation of application No. 09/352,281, filed on Jul. 13, 1999, now Pat. No. 6,156,178.

(51) Int. Cl.⁷ .......................... B01D 57/02; C02F 1/40; G01N 21/00; C12Q 1/68; C12P 19/34
(52) U.S. Cl. .................. 204/457; 204/450; 204/453; 204/456; 204/604; 356/344; 435/6; 435/91.2
(58) Field of Search .................. 204/457, 450, 204/453, 456, 604; 356/344; 435/6, 91.2

(56) References Cited

U.S. PATENT DOCUMENTS

| | | | |
|---|---|---|---|
| 4,683,202 A | | 7/1987 | Mullis |
| 4,911,807 A | | 3/1990 | Burd |
| 5,798,032 A | | 8/1998 | Khan et al. |
| 5,843,660 A | | 12/1998 | Schumm et al. |
| 5,846,710 A | | 12/1998 | Bajaj |
| 5,885,775 A | | 3/1999 | Haff et al. |
| 5,888,819 A | | 3/1999 | Goelet et al. |
| 6,156,178 A | * | 12/2000 | Mansfield et al. .......... 204/450 |

FOREIGN PATENT DOCUMENTS

| | | |
|---|---|---|
| EP | 0864860 A1 | 9/1998 |
| WO | WO99/22228 | 5/1999 |
| WO | WO99/34203 | 7/1999 |

OTHER PUBLICATIONS

K. Mitchelson et al., "The Use of Capillary Electrophoresis for Point Mutation Screening", *Trends Biotechnol.*, Nov. 1997, 15(11):448–51.

Piggee et al., "Capillary Electrophoresis for the Detection of Known Point Mutations by Single–Nucleotide Primer Extension and Laser–Induced Fluorescence Detection", *Journal of Chromatography* A 781 (1997), pp. 367–375.

Hoogendoorn et al., "Genotyping Singly Nucleotide Polymorphisms by Primer Extension and High Performance Liquid Chromatography", *Human Genetics* (1999) 104:89–93.

Simpson et al., "High–Throughput Genetic Analysis Using Microfabricated 96–Sample Capillary Array Electrophoresis Microplates", *Proceedings of the National Academy of Sciences*, Mar. 1998, vol. 95, pp. 2256–2261.

Krook et al., "Rapid and Simultaneous Detection of Multiple Mutations by Pooled and Multiplex Single Nucleotide Primer Extension: Application to the Study of Insulin–Responsive Glucose Transporter and Insulin Receptor Mutations in Non–Insulin–Dependent Diabetes", *Human Molecular Genetics*, vol. 1, No. 6, pp. 391–395.

Ross et al., "High Level Multiplex Genotyping by MALDI–TOF mass spectrometry", *Nature Biotechnology*, vol. 16, Dec. 1998.

Hooker et al., "A Transparent Flow Gating Interface for the Coupling of Microcolumn LC with CZE in a Comprehensive Two–Dimensional System", *Analytical Chemistry*, vol. 69, No. 20, pp. 4134–4142 (Oct. 15, 1997).

Woolley et al., "Functional integration of PCR amplification and capillary electrophoresis in a microfabricated DNA analysis device", *Analytical Chemistry*, vol. 68, No. 23, pp. 4081–4086 (Dec. 1, 1996).

* cited by examiner

Primary Examiner—Kenneth R. Horlick
Assistant Examiner—Young Kim
(74) Attorney, Agent, or Firm—Thomas Schneck; David M. Schneck

(57) ABSTRACT

The apparatus and method of the present invention disclose a system in which multiple injections may be made into a capillary array. The injections are spaced in time with each injection followed by an interval of electrophoresis. Once all samples are loaded into the capillaries, continuous electrophoresis and detection is used to separate and detect target compounds within the sample. The interval between injections is matched to the target compound migration rate to be sufficient to allow the target compounds to be detectably separated when the compounds reach the detector.

7 Claims, 7 Drawing Sheets

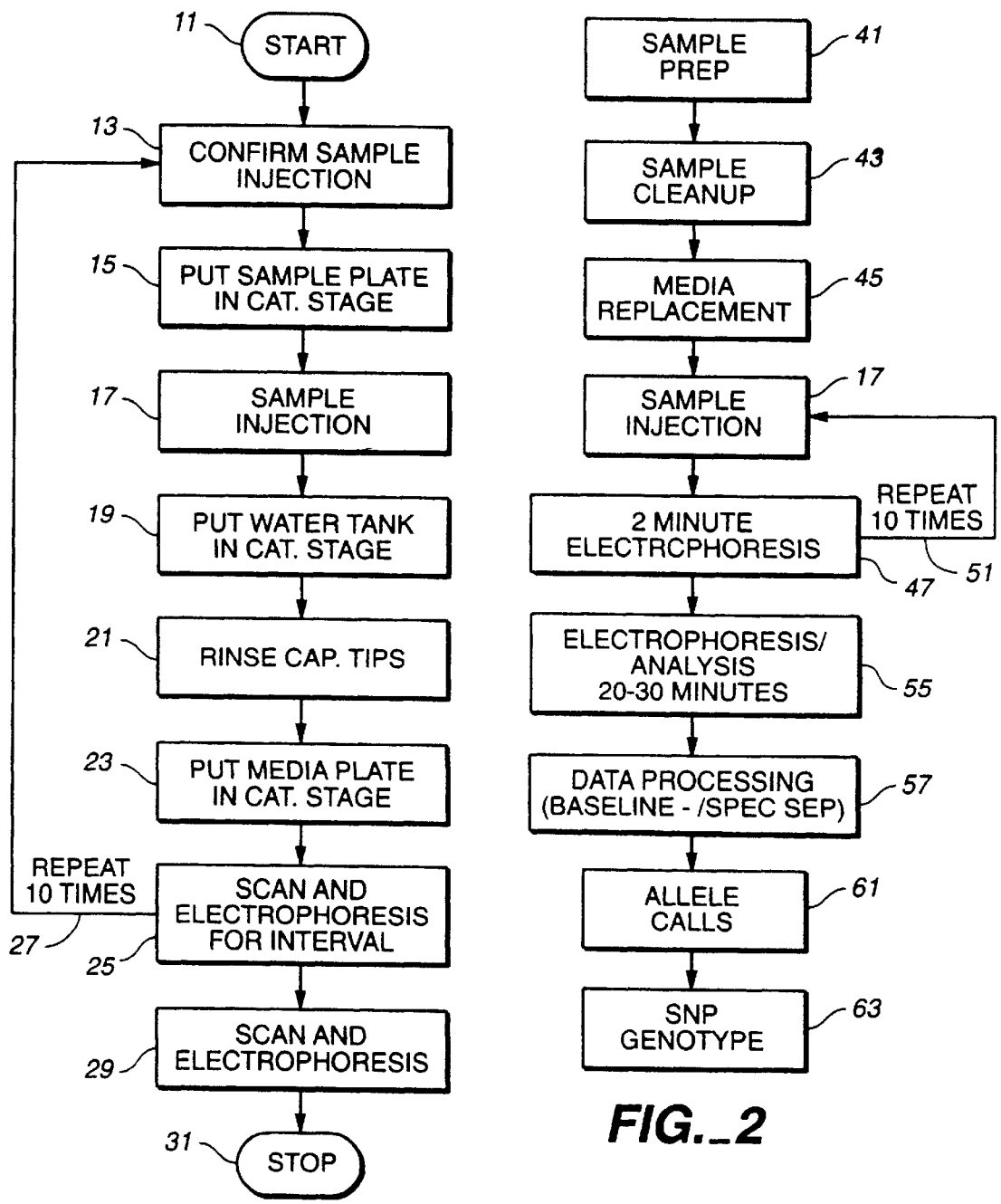

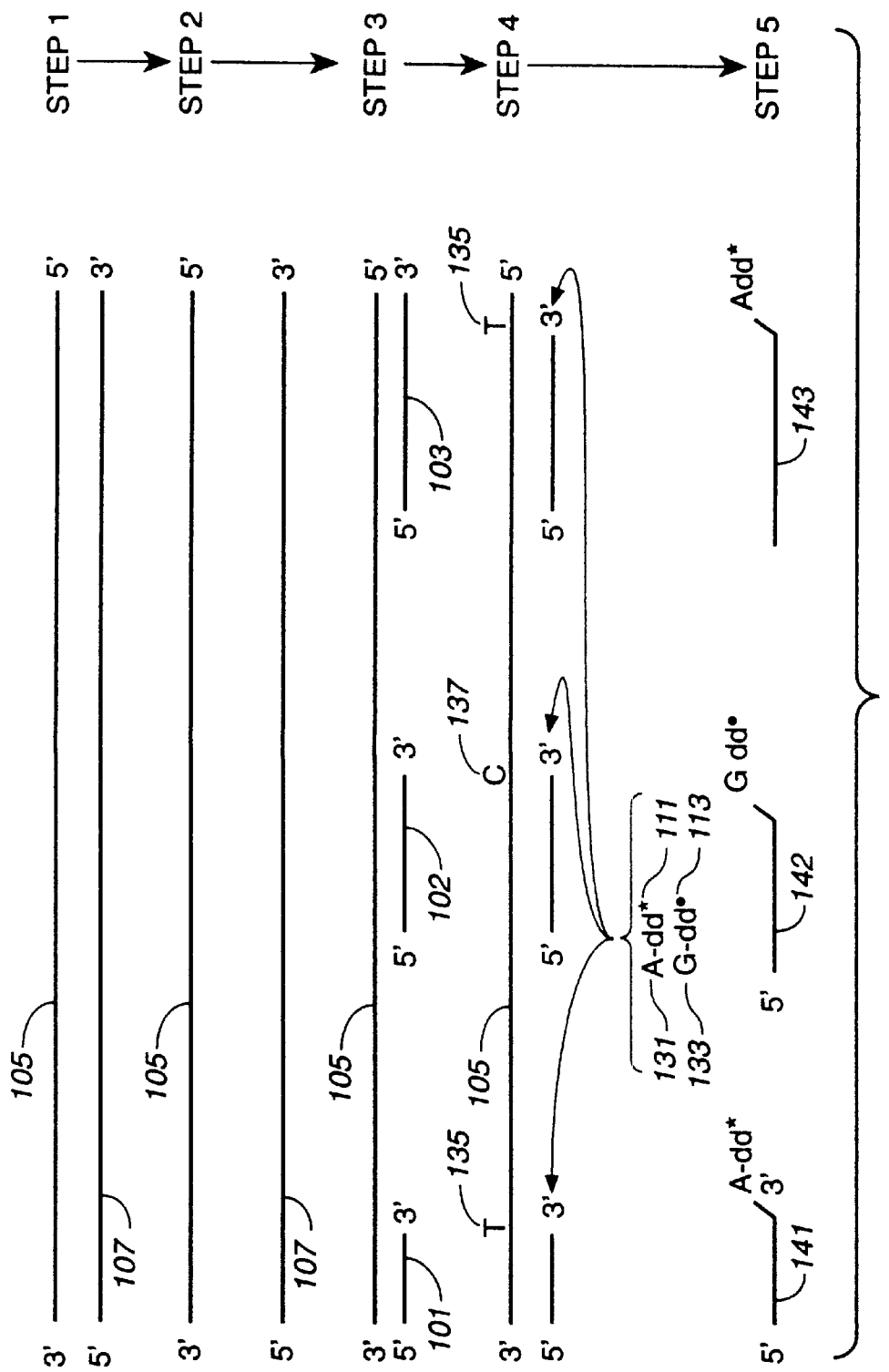
FIG._3

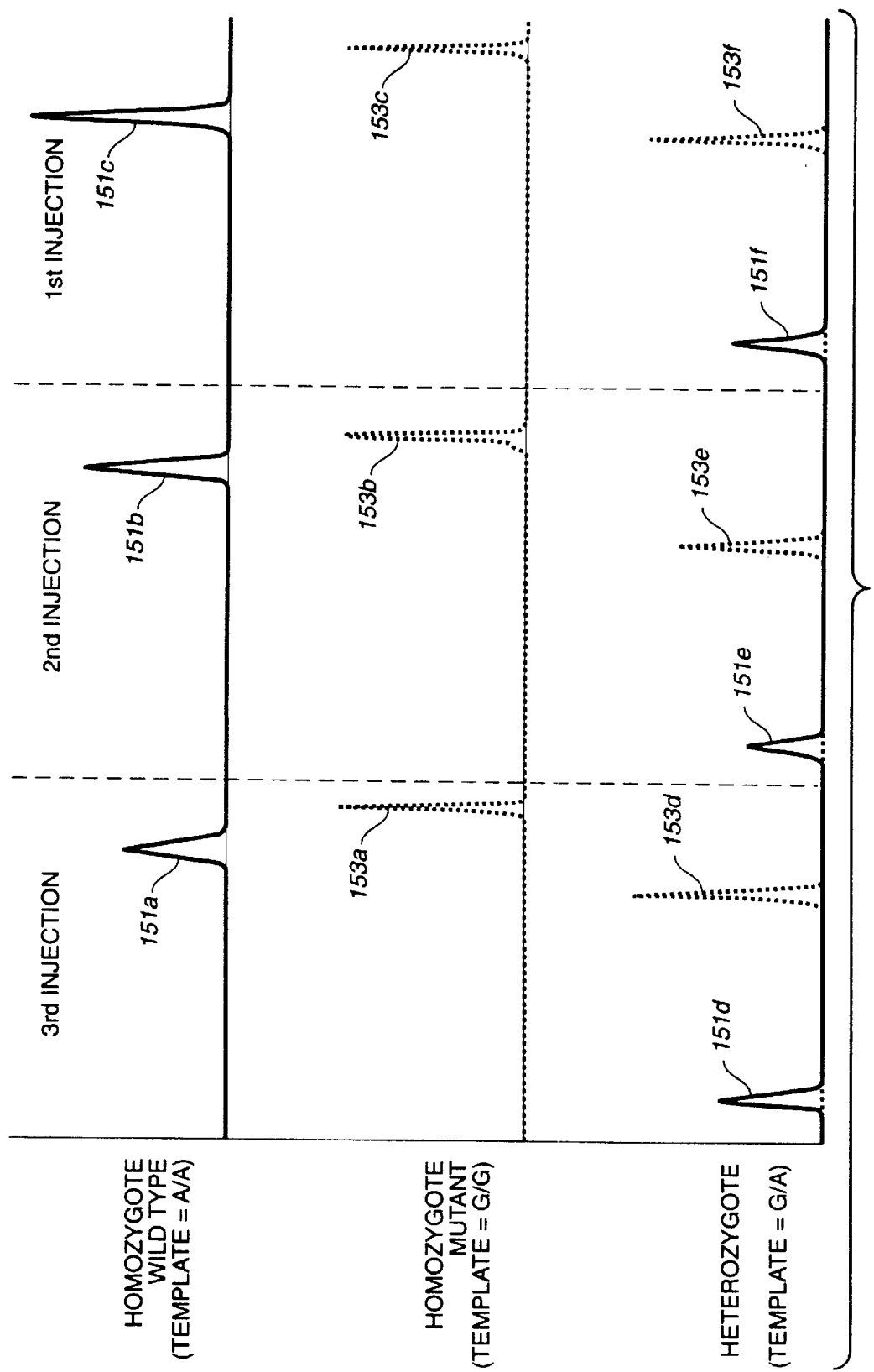
FIG._4

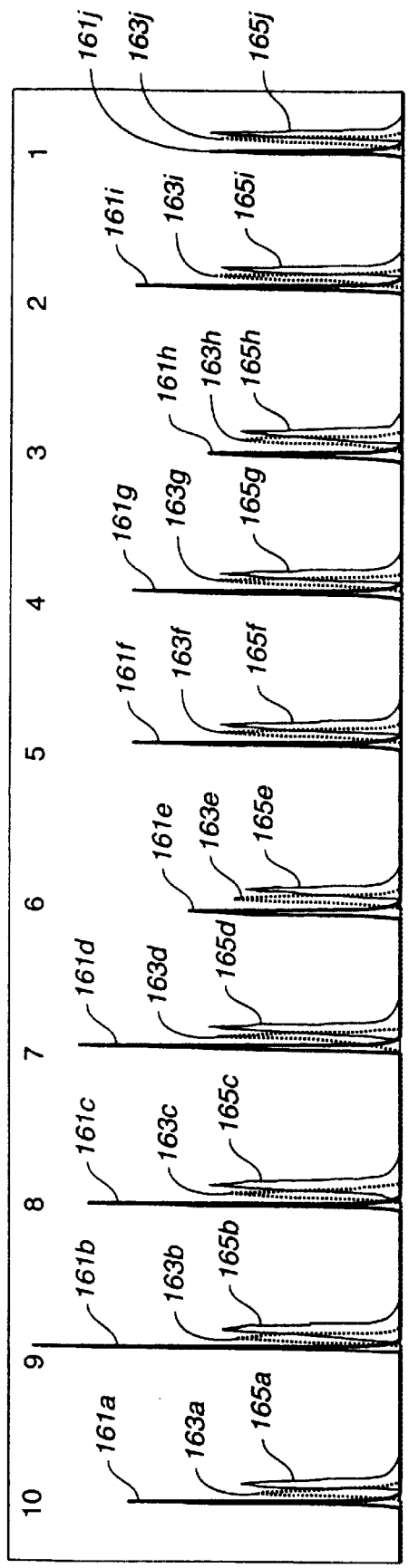
FIG._5

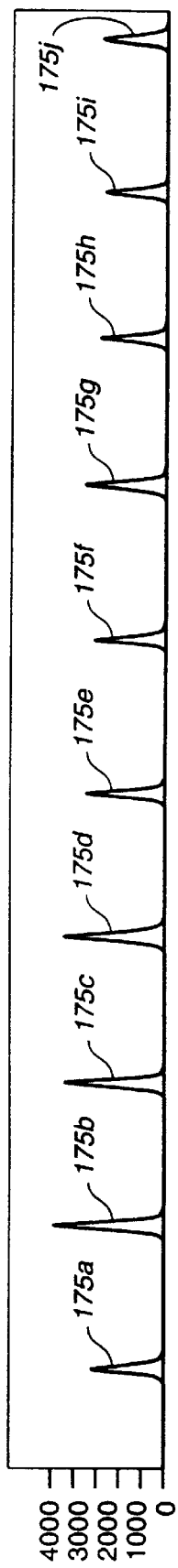
FIG._6A
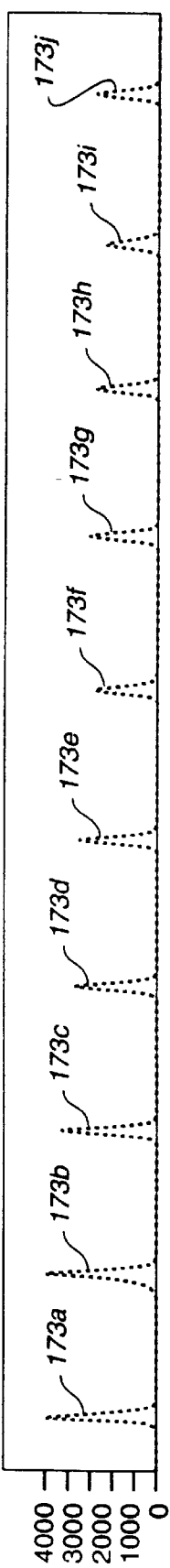
FIG._6B
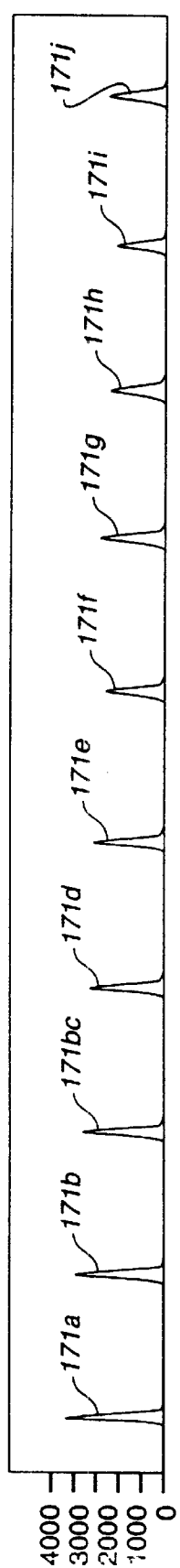
FIG._6C
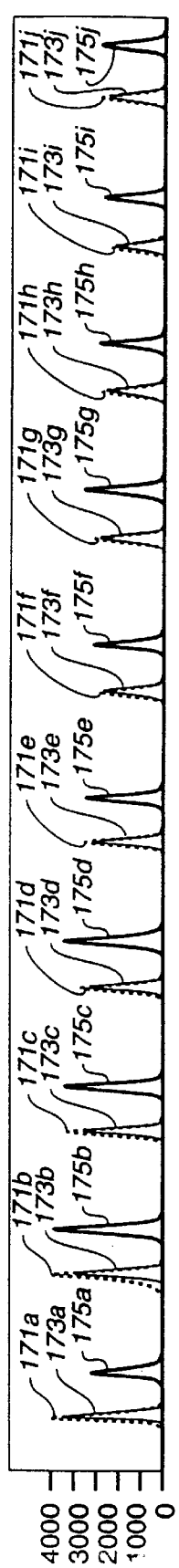
FIG._6D

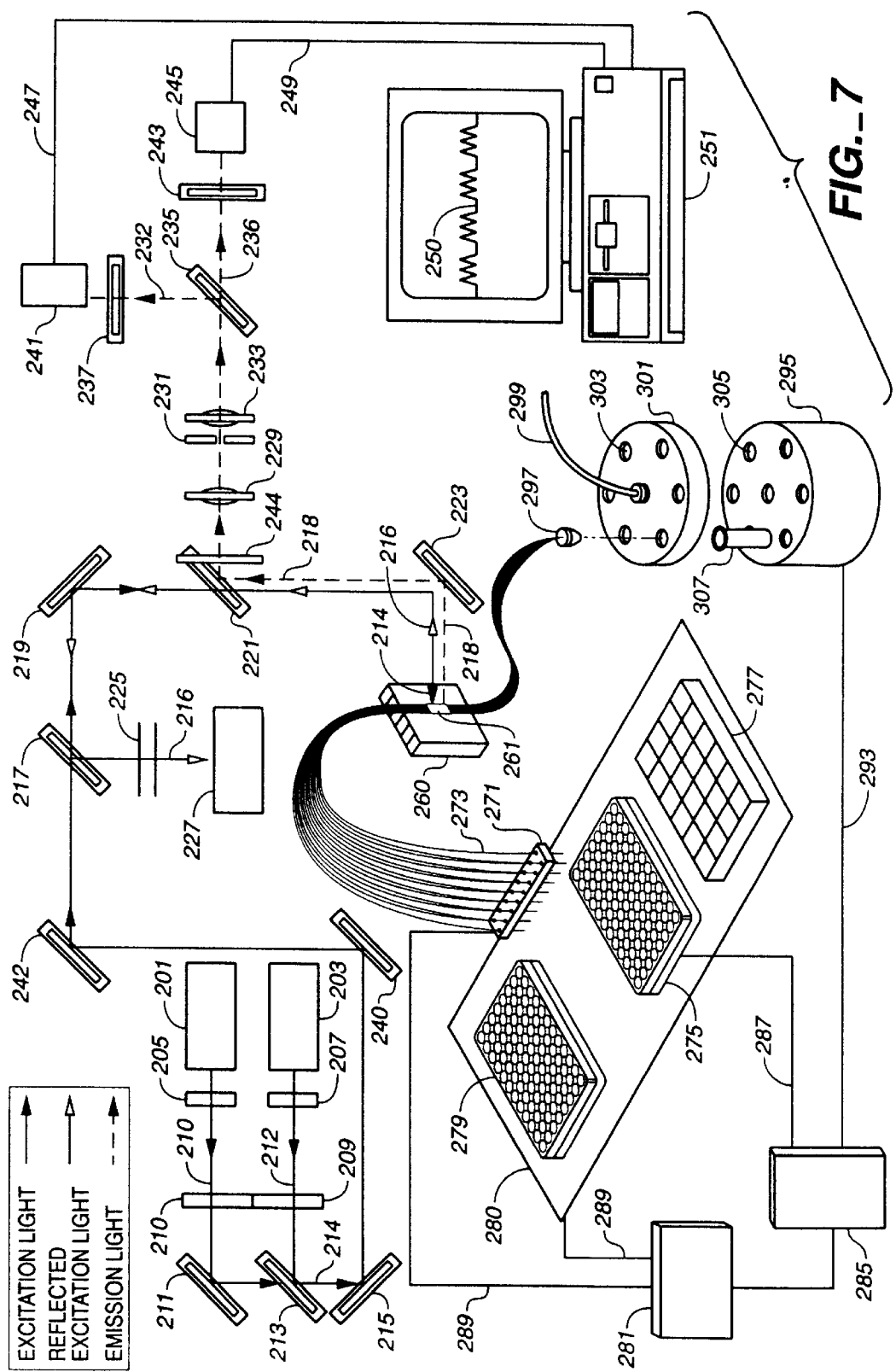
FIG._7

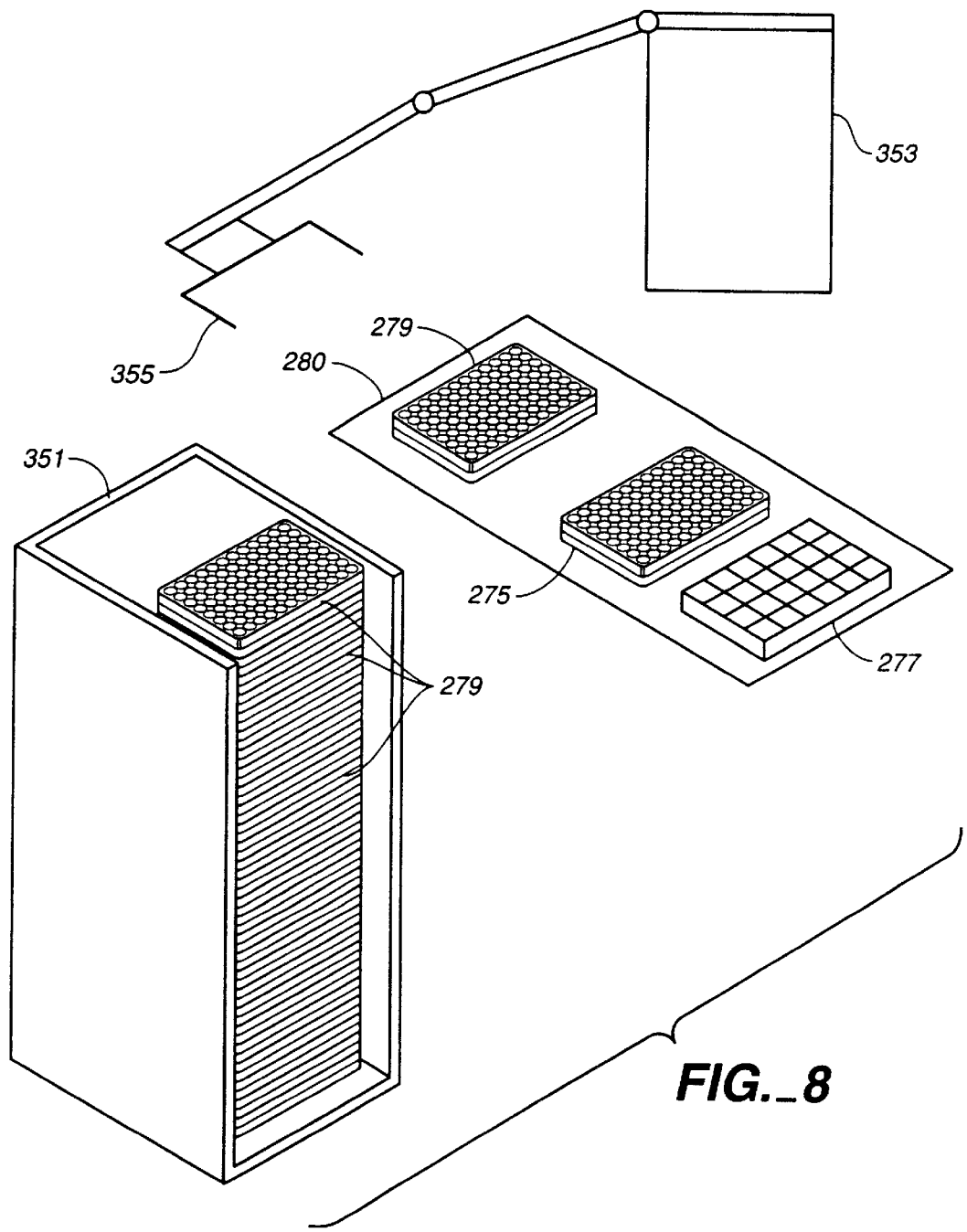
FIG._8

INCREASED THROUGHPUT ANALYSIS OF SMALL COMPOUNDS USING MULTIPLE TEMPORALLY SPACED INJECTIONS

CROSS-REFERENCE TO RELATED APPLICATIONS

This application is a continuation of U.S. patent application Ser. No. 09/712,013 filed Nov. 13, 2000 now abandoned which is a continuation of U.S. patent application Ser. No. 09/352,281 filed Jul. 13, 1999, now U.S. Pat. No. 6,156,178 granted Dec. 5, 2000.

FIELD OF THE INVENTION

This invention relates to method and apparatus for increasing the throughput of analysis of compounds of a discrete size range.

BACKGROUND OF THE INVENTION

The references mentioned herein are expressly incorporated by reference.

Separation of compounds is key to sample analysis in biology, chemistry, and physics. In numerous linear type (two-dimensional) separation systems, compounds are introduced into one end of a separation length and a flow force is then applied separating the compounds. Once the compounds are separated, the compounds can then be detected, analyzed and possibly isolated. Such separation systems include chromatography, electrophoresis, and centrifugal separation systems.

The very large number of compounds that need to be separated and analyzed has led to an increasing emphasis on high throughput systems. High throughput systems utilize automation, miniaturization, and parallel reactions or separations to increase the speed at which samples may be analyzed. This allows for an assay to maximize the information gained while minimizing the resources required to effect analysis. This achieves the benefit of lowering the amount of material required for each reaction, maximizing the value of costly analytical equipment, and efficiently using experimentalist time.

A number of fields require increased throughput systems. Environmental sampling, combinatorial chemistry, genomic assay and other fields require very large numbers of samples to be analyzed. High throughput analysis is also increasingly important to the analysis of nucleic acid sequences.

The development of the ability to generate very large numbers of discrete length oligonucleotide in samples has increased the demand for high throughput of oligonucleotide analytical systems. The polymerase chain reaction (PCR) (described in U.S. Pat. No. 4,683,202 to Mullis, K. et al.) discloses a method for amplification of nucleic acid sequences. In this method, high copy numbers of single strands of template nucleic acid sequences are generated. A short nucleic acid sequence primer is annealed to a specific sequence of the single stranded template nucleic acid. An initiator (DNA polymerase) adds nucleotide bases from solution to the 3'-end of the primer. By using matched sets of two primers, oligonucleotide products of specific known length may be amplified. In addition to PCR, use of restriction enzymes to cut nucleic acid strands into fragments of discrete lengths is used to detect specific sequence differences in DNA.

An additional need for high throughput nucleic acid analytical systems results from the very large size and variability of the genomes of various organisms. For example, human genome contains over three billion nucleotide base pairs. These three billion bases represent many thousands of genes. When analyzed on the base pair level, millions of single base variations exist in the human population. High throughput is required for systems used to analyze genomic variation of an organism or to track segregation within a genome.

Various methods can be used to detect genetic variability. These include restriction fragment length polymorphism (RFLP), analysis of short tandem repeat (STR) loci, and analysis of single nucleotide polymorphism.

RFLP is an assay for variation in DNA sequences at a site at which a particular restriction enzyme cuts. DNA variants will give different sizes of DNA fragments after digestion with a specific restriction enzyme. The use of probes to detect known sequences allows determination of restriction site variability proximate to a specific locus. RFLP can be combined with PCR to produce oligonucleotides of a discrete size range. In "The use of capillary electrophoresis for point mutation screening" in Trends Biotechnol., November 1997; 15(11):448–51 by Mitchelson, K.; Cheng, J.; Kricka, L., the authors described the widely used PCR-RFLP technique wherein the PCR reaction is run to produce amplified DNA fragments from a target template DNA. The amplified product is cleaved by a restriction endonuclease at specific cleavage sites to which the endonuclease binds and the size of resulting fragments determined. Presence or absence of a cleavage site is indicative of detection of the mutation of interest.

Short tandem repeat loci (variation in the number of short, tandem repeat units at a locus causing DNA length variability between alleles at that locus) may be used to assay DNA variability. The highly variable copy number of the short repeats serves as a genetic marker. Distinct polymorphic short tandem repeat (STR) loci are amplified and analyzed. U.S. Pat. No. 5,843,660 to Schumm et al. describes a procedure for using PCR to amplify STR loci. The amplification procedure produces a set of nucleic acid fragments within a discrete size range. The nucleic acid sequences of the discrete size range may then be separated and analyzed. In addition to RFLP and STR, single nucleotide polymorphisms may be used as markers of the genetic or phenotypic variability and as genetic markers. The use of single nucleotide polymorphism may present various advantages over either RFLP or STR analysis.

Numerous advantages are presented by single nucleotide polymorphism (SNP) analysis. Generally SNP analysis protocols produce small nucleic acid sequences of a discrete size range. SNP analysis may be rapid and adaptable to automation. This results in a reduction of the amount of reagents and other materials that is needed to effect this analysis. SNP genotyping is highly adaptable to high throughput systems. In the human genome, millions of individual single nucleotide polymorphisms exist. In contrast, much lower frequency of STR or RFLP variants occur.

The advantages of SNP analysis have made this analysis a preferred genomic marker assay. SNP analysis is useful for genotyping or enabling mutation scoring, genetic mapping, pharmacogenetic typing, phylogeny typing, and is adaptable to forensic and identity analysis. Single nucleotide polymorphisms may correlate to phenotypic expression and some SNP variants could serve as markers for disease states enabling simplified diagnostics. A relatively large number of SNP variants exist in the human genome, numbering in the millions. At specific loci, the variation may be between two nucleotides: a common-type variant nucleotide (common variant allele) and a rare-type variant nucleotide (rare variant allele). This binary variation (diallelic) enables allele analysis in which a variant may be categorized as either primary type or variant type. Thus unlike STR variation, SNP variation more rapidly may yield binary allele calls. RFLP variants are binary but cumbersome and expensive.

A number of techniques have been described to use single nucleotide polymorphism in genetic analysis. One such procedure is single nucleotide primer extension (SNuPE). An example is seen in U.S. Pat. No. 5,888,819 to Goelet et al. which describes the use of a PCR-like analysis system to gain information on genetic variation. In this procedure a single stranded template nucleic acid sequence is obtained and a primer is hybridized onto a conforming template sequence to form a template-primer duplex. A DNA polymerase extends the nucleic acid-primer duplex by one nucleotide. This can be enabled by using a terminator, such as a radio-labeled or fluorescence-labeled dideoxynucleotide, to ensure that only a single base is attached to the 3'-end of the primer. This protocol extends the primer by one base. Determination of which type of nucleotide was incorporated onto the 3'-end of the primer is enabled by the presence of the type of the detectable label.

U.S. Pat. No. 5,846,710 to Bajaj describes similar technology for single nucleotide polymorphism analysis. A single stranded sample oligonucleotide is mixed with a labeled nucleotide, a primer having a sequence complementary to a known sequence on the template oligonucleotide and an agent to induce DNA extension (such as a DNA polymerase). Other than the labeled nucleotide, no other nucleotides are included in the mixture. The mixture is then subjected to conditions under which the primer anneals to the sample single stranded oligonucleotide. The DNA polymerase then incorporates the labeled nucleotide if a base complementary to the labeled nucleotide is present at the location on the sample oligonucleotide at the single base opposite the base immediately upstream of the 3'-end of the primer. An article entitled "Capillary Electrophoresis for the Detection of Known Point Mutations by Single-Nucleotide Primer Extension and Laser-Induced Fluorescence Detection" by Piggee, C. et al. in Journal of Chromatography A 781 (1997), p. 367–375 describes the separation of DNA fragments in a capillary electrophoresis format in conjunction with laser-induced fluorescence (LIF) detection. LIF was used to detect single nucleotide polymorphism using a method of single-nucleotide primer extension described in the previous two references. The labeled terminator was labeled with fluorescent dyes.

A number of different methods of analyzing single nucleotide polymorphisms by using single nucleotide primer extension reactions with detection of the resultant reaction products have been described. In Human Genetics (1999) 104:89–93, author Hoogendoorn, B. et al. in an article entitled "Genotyping Single Nucleotide Polymorphism by Primer Extension and High Performance Liquid Chromatography" describes SNuPE reaction product analysis using high performance liquid chromatography (HPLC). This reference describes a "minisequencing" type analysis wherein a DNA sequence containing a single nucleotide polymorphism is amplified by the extension of an oligonucleotide primer which is annealed adjacent to the polymorphism. In the presence of a labeled terminator, the primer is extended by at least one base. In the PCR reaction mixture is included at least three of the four nucleotides and one terminator nucleotide. A DNA polymerase will add nucleotides to the 3'-end of the primer to a location on the sample DNA complementary to the terminator base. HPLC analysis of the primer extension reaction products from such a reaction results in chromatographic data from which the genotype of the polymorphic site, with genotype cells as a wild type or mutant type.

U.S. Pat. No. 5,885,775 to Haff et al. describes methods for single nucleotide polymorphism analysis by mass spectrometry. As in the previous methods, a PCR reaction including a nucleotide terminator generates a primer extension product of a discrete size range. The base composition of the extended primer is determined by mass spectrometry. The different weights of the various nucleoside bases allow the bases to be distinguished.

In many of these DNA analytical methods, a large number of oligonucleotides of a discrete size range are generated and analyzed. Various techniques may be adapted to increase the throughput of the analysis of the compounds. The use of high throughput techniques allows for the analysis of nucleic acid sequences at a faster rate.

Various techniques have been adapted to increase the throughput of the analysis of small compounds (e.g. nucleic acid sequences in a discrete size range). In Proceedings of the National Academy of Sciences, vol. 95, pages 2256–2261, March 1998 in an article entitled "High-throughput genetic analysis using microfabricated 96-sample capillary electrophoresis microplates" by Simpson, P. et al., the authors disclose a capillary array electrophoresis system that can rapidly analyze 96 samples in a parallel electrophoresis procedure. This system utilizes a 96-sample well glass sandwich microplate with 48 separation channels. Two machined capillaries flow into each channel. Samples are injected into two ports on two capillary lengths which lead to a central detector. This permits the serial analysis of two different samples in each associated capillary with detection by a central detector. This technique requires the specialized microplate sample well with injection unit to produce the increased throughput. Multiple injection reservoirs and capillaries are required for the serial injection of two samples to be read by one detector.

Additional methods to increase throughput of genomic analysis are described in Human Molecular Genetics, volume 1, no. 6, page 391–395 in an article entitled "Rapid and Simultaneous Detection of Multiple Mutations by Pooled and Multiplexed Single Nucleotide Primer Extension: Application of the Study of Insulin-Responsive Glucose Transporter and Insulin Receptor Mutations in Non-Insulin-Dependent Diabetes" by Krook, A. et al. In this publication, the authors describe two techniques employed in single nucleotide primer extension reactions that allow greater throughput by simultaneously examining multiple alleles at multiple loci.

The first technique described is the pooling of samples. By adding together a large number of samples prior to performing PCR reactions for a single locus allows for analysis of a large amount of samples in a single nucleotide primer extension reaction. This technique is most useful for the analysis of rare type alleles. If an analysis of the pool indicates the presence of a target sequence within the pool of samples, individual samples may be later analyzed to determine the individual containing the sequence of interest.

The second adaptation to increase throughput is the use of multiple primers of varied length during primer extension. Each primer is designed to bind to a specific known sequence with a polymorphic genetic variant positioned at the base located immediately downstream opposite the 3'-end of the primer. Using several primers of distinguishably different lengths allows throughput to be increased. A similar technique of increasing throughput is described in Nature Biotechnology, Vol. 16, December 1998 in an article entitled "High Level Multiplex Genotyping by MAODI-TOF Mass Spectrometry" by Ross, E. et al. This reference describes the use of a 12-primer system to analyze single nucleotide polymorphism at 12 different loci. The twelve primers are combined in a single PCR reaction. The reaction products are analyzed by mass spectrometry. The primers are of sufficiently different length to allow them to be distinguished by mass spectrometry.

An additional method to increase throughput is by the use of multiple dye labels. Attaching a dye having a specific characteristic excitation and emission wavelength to each nucleotide terminator used in a SNuPE reaction allows the simultaneous analysis of nucleotide variation. An optical detector can simultaneously distinguish the various wavelengths of each dye thereby detecting the specific nucleotide incorporated in the analyzed oligonucleotide.

It is the object of the invention to describe a technique and apparatus for further increasing the throughput of analytical systems designed to analyze small compounds, particularly DNA sequences of a discrete size range.

It is a further object to effect this increase in throughput with limited alteration to existing apparatus.

SUMMARY OF THE INVENTION

The above objects have been achieved through a method and apparatus in which injections into a separation length are spaced in time, with this spacing designed such that the separate injections are detectably separated at a detection location along the separation length distal from the sample injection location. The timing of the injection is designed such that when samples reach the detector, the samples are detectably separated and the compounds within each sample are likewise detectably separated.

As applied to capillary electrophoresis providing an array of capillaries and filling each capillary in the array with a separation media effects this method. The separation media may include a sieving matrix or may be a free solution capillary electrophoresis media. The method further includes preparing a plurality of samples wherein a percentage of the plurality of samples contains a target molecule of a discrete size range. Each different target molecule is labeled with a characteristic detectable labeling agent. The plurality of samples may be prepared or amplified in a number of ways including utilizing the polymerase chain reaction to produce oligonucleotides of a distinctive size range. In effecting the polymerase chain reaction, the use of multiple primers, pooling of samples, and multiple optically detectable labeling agents allows for an increase in throughput of sample analysis. The step of preparing a plurality of samples may include using single nucleotide primer extension to assay single nucleotide polymorphism at one or more loci in each separate sample preparation.

After the samples are prepared or amplified, they are transferred into a plurality of sample receptacle containers. Each sample receptacle container has a plurality of sample holding receptacles for holding the sample. An example of a sample receptacle container is a 96-well microplate. Each capillary in the capillary array is brought into contact with one sample in the sample receptacle container. A discrete selected amount of the sample may then be loaded into each capillary by an injector.

The samples are loaded in a batch, each batch representing the samples from a single sample receptacle container. The samples are then electrophoretically separated. The electrophoretic separation causes the samples to migrate away from the injector and towards a detector. After the samples have migrated a selected distance away from the injector, the injector injects another sample into each capillary in the array of capillaries from another sample receptacle container. The cycle of injection and separation is repeated a number of times. The array of capillaries is scanned at a detection region to detect the labels on the small target molecules that have been separated. This produces detection data that may then be analyzed.

The method uses the additional step of the inclusion with the samples of a quality metric standard. Such a standard could provide information on the efficacy of the sample separation, the functioning of the sample separation system, or the size of the compound being analyzed.

An alternative aspect of the invention is an apparatus for the ultra high throughput analysis of small compounds. The apparatus includes a capillary array with each capillary of the array filled with a separation media. Electrodes may be brought into electrical communication with the opposing ends of each capillary introducing electrical flow through the capillary. An injector is configured to inject samples from a multiwell sample plate into an injection end of each of the capillaries in the array. Associated with the injector is a timer that periodically instructs the injector to inject additional samples from additional multiwell plates into the capillaries of the capillary array. The capillary array has a detection area associated with the capillaries of the capillary array at an end distal from the injection end. A laser in the apparatus directs coherent light at the detection area that excites fluorescence from labeled samples within the capillaries. A multi-channel optical detector is positioned to detect this excited fluorescence.

The timer that is included with the apparatus may also be associated with the electrodes such that before the timer instructs the injector to inject additional samples into the capillary array, the timer first instructs the electrodes to pause the current flow through the capillary array. This timing system may be a circuit, a timing algorithm or some other timing means.

The apparatus may also include a multiwell sample plate transporter such as a conveyor or robotic arm to bring additional multiwell sample plates to the injector and a magazine for feeding the multiwell sample plates to the transporter.

BRIEF DESCRIPTION OF THE DRAWINGS

FIG. 1 is a flow chart of the steps of the high throughput sample analysis method of the present invention as embodied in a capillary array electrophoresis system.

FIG. 2 is a flow chart showing the steps of high throughput sample analysis using a capillary array electrophoresis system to analyze single nucleotide primer extension reaction products.

FIG. 3 is a schematic illustrating the single nucleotide primer extension method of sample preparation.

FIG. 4 is a data of laser induced fluorescence detection in a capillary electrophoresis system of different allelic states measured from multiple injections over time.

FIG. 5 shows data from a 10-injection capillary electrophoresis analysis of samples, the samples containing two compounds each labeled with optically detectable label and a third optically detectable quality metric standard.

FIG. 6A shows data gathered at a first wavelength from a 10-injection capillary electrophoresis analysis.

FIG. 6B shows data gathered at a second wavelength as in FIG. 6A.

FIG. 6C shows data gathered at a third wavelength as in FIG. 6A.

FIG. 6D shows an overlay of the data of FIGS. 6A, 6B and 6C.

FIG. 7 is a plan view of an apparatus with a timer to effect the injections over time into an array capillary electrophoresis system.

FIG. 8 is a plan view for a robotic transfer system that moves sample containers from a magazine to the cathode stage.

DETAILED DESCRIPTION OF THE INVENTION

The invention should be understood using the following definitions.

allele: one of the two or more alternate genetic sequences occupying the same chromosomal locus.

homozygous: having two identical alleles in a pair of homologous chromosomes.

heterozygous: having two different alleles in a pair of homologous chromosomes.

electrophoretic media: a liquid or gel through which electrical current may flow and compounds may be electrophoretically separated.

free solution capillary electrophoresis media: electrophoresis media with substantially no matrix effects, polymer network, imposed pH gradient, or secondary phase such that greater than 90% of the separation is a result of the compound's net charge.

low viscosity media: media with a viscosity of 5000 centipoise or less.

small compounds/small molecules: a compound or molecules with a weight of 33,000 dalton or less.

allele calls: determination of allele state at specific loci.

single nucleotide polymorphism: variation in a single nucleotide at a specific locus.

Scientific analytical instrumentation, including centrifugal, chromatographic, and electrophoretic separation systems rely upon separation of compounds along a separation length. Once the samples have been separated by a separation force, the target compounds within the sample may be detected and/or collected. Increase in system throughput enables efficient use of instrumentation and experimentalist time. In the present invention, throughput is increased by injecting multiple samples onto the separation length, with the injection of samples into the separation length spaced over time such that when the samples reach a detector the target compounds within the sample are detectably separated. Additionally the injection interval must be sufficient to prevent one sample from migrating into another sample. Such determination may be made if the sample migration rate along the length is known.

Capillary electrophoresis is one example of an analytical method adaptable for use with multiple injections over time. This method is most useful for the high throughput analysis of small compounds such as nucleic acids, proteins or other compounds produced that are of a small discrete known size range. Because the relative size range of the compounds is known, the migration rates of the compounds may be determined. For example, the electrophoretic mobility of a particle in a free solution capillary electrophoresis system may be determined by the formula:

$$\mu = q/f$$

where $\mu$=electrophoretic mobility, q=particle net charge, f=translational friction coefficient.

By using this formula, the electrophoretic mobility of the target compound may be approximated allowing for measurement of the migration rate. Once the migration rate is known, the minimal required spacing between samples can be determined. It is also possible to determine minimal sample injection experimentally.

The flow chart in FIG. 1 illustrates a method of spacing injections into a capillary array electrophoresis system over time to increase analytical throughput. The capillary array electrophoresis is comprised of a plurality of capillaries, with each capillary filled with a separation media. A first end of each capillary in the array is adapted for sample injection. The injection ends of the capillary are held in a cathode block with a defined spacing to a detection area associated with each capillary located at the distal end of each capillary. The system effects electrophoresis by placing the injection end of each capillary in electrical communication with a cathode and placing an opposite end of each capillary in electrical communication with an anode.

At the start of the procedure (block 11) a plurality of microplates are provided. The wells in each microplate contain a prepared sample. A portion of the samples may contain small target compounds. These target compounds migrate at a known rate or within a known range of rates.

After the plurality of microplates containing the assay samples has been prepared, the electrophoresis process begins. The initial step is confirmation of sample injection (block 13). As the first plate is loaded, the procedure confirms that an initial sample is yet to be injected. The sample plate is then moved to the cathode stage (block 15). Once the sample plate is in the cathode stage, the capillaries in the array of capillaries are each introduced into a well on the sample-containing microplate. Once the capillaries are in contact with the sample, the sample injection (block 17) occurs. Sample injection introduces a discrete amount of sample from each well of the sample-containing microplate into an individual associated capillary. Several methods of sample injections are possible. These methods include using a pulse of electrical current to cause a discrete amount of sample to migrate into the capillaries. It is also possible to pressure inject a discrete amount of sample into each capillary.

Once the samples are injected, a water tank is moved onto the cathode stage (block 19). The capillary tips of the capillary array are then rinsed in the water tank (block 21). Alternately, the capillary tips may be directly rinsed with buffer. This removes any excess sample from the exterior of the capillary tubes in the array preventing cross-contamination. After the capillary tips are rinsed, the media plate is moved into the cathode stage (block 23). The media plate is linked to a power source. With the media plate in place, electrical current can flow through the array of capillaries.

With the media plate in place, electrical current may flow through the capillaries. This will cause electrophoretic separation of the target compounds with the compounds migrating through the capillary from the cathode to an anode end. As the electrophoresis occurs, a scanning mechanism scans an area of the capillary distal to the injection end of the capillary (or the ends of the capillaries in sheath flow systems). The scan is continuous during the electrophoretic separation.

The electrophoretic separation of compounds with simultaneous scanning of a detection area occurs for a determined interval (block 25). The length of the interval is sufficient to migrate the sample away from the injection end of the capillary. Once this interval has occurred, the steps shown in blocks 13, 15, 17, 19, 21, 23, 25 are repeated ten times (arrow 27). The spacing of the samples is such that the target compounds within each sample do not migrate at a rate such that the samples are not distinguishable when the target compounds reach the detection area. The length of the capillaries used in the array of capillaries is sufficient in length to allow 10 samples to be injected and separated for a determined interval without the first injected sample reaching the detector. Thus all samples are loaded onto the capillary before any sample is detected.

After all of the samples have been loaded onto the capillary, continuous electrophoresis causes the target compounds within the samples to migrate from a cathode end of the capillary to an anode end. Distal from the injection end of the capillary is a detection area associated with the capillary. As target compounds pass the detection area, the compounds are detected. Thus continuous scan and electrophoresis (block 29) is effected for sufficient time to allow all of the samples within the capillary tube to migrate past the detection area and be scanned. After all of the samples have migrated past the detection area, the procedure stops (block 31).

FIG. 2 presents a more detailed view of use of multiple injections spaced over time with a capillary array electrophoresis system to separate nucleic acid fragments of discrete size. The separated nucleic acid sequences shown in FIG. 2 are directed to detect single nucleotide polymorphism a specific locus. The initial step requires preparation of samples (block 41). The sample preparation includes single nucleotide polymorphism assay. This assay could be single nucleotide primer extension reactions, polymerase chain reaction, or other sample preparation methods. Further detail about sample preparation method is discussed in conjunction with FIG. 3. The sample preparation creates a number of samples with a percentage of the samples containing target compounds. In this example, the target compounds are nucleic acid sequences of a discrete size range. Since the size range of the target compounds is known, the rate of electrophoretic migration of targets can be determined. Once the sample nucleic acid sequences are generated, the sample is then purified (block 43) to remove salts or other contaminants. Sample cleanup allows the target compounds to be purified and template DNA and excess detectable labels or excess nucleotides to be removed. Sample cleanup may require a procedure to desalt the target compounds allowing more efficient electrophoretic separation. The samples are each placed in a well on a multiwell sample plate.

The electrophoretic separation procedure begins by replacing the media within the capillary (block 45). The media can be the free solution capillary electrophoresis media or alternatively may be a matrix for sieving various sized compounds. In a free solution capillary electrophoresis media, such as 4.5% or less hydroxyethyl cellulose (HEC), the media has substantially no matrix effects, polymer network, imposed pH gradient, or secondary phase. This results in substantially all (90% or greater) of the migration as a result of the net charge of the compound in the electrical field. In contrast, in sieving media, such as linear or crosslinked acrylimide, the separation media serves a sieving function where compound size is a significant factor in particle migration rate. If a low viscosity media is used, pressure filling may not be required. The media can be drawn in by lower pressure or by capillary action. The media is pressure filled into the capillaries. Linear polyacrylimide at a concentration of 4% or less also is an effective separation media.

Once the capillaries have been filled with media, the first sample is injected (block 17). As was seen in FIG. 1 the sample may be injected by using a brief pulse of current, by pressure injection or by other known injection methods. Following injection, current is introduced through the capillary for a two minute interval to migrate the sample away from the injection area towards a detection end of the capillary (block 47). After the two-minute electrophoresis interval a subsequent sample is injected. This process of sample injection followed by two-minute electrophoresis is repeated 10 times as indicated by arrow 51. The length of the capillaries in the array of capillaries in this method is selected such that the 10 samples may be injected into each capillary followed by two-minute electrophoretic separation without having the initial sample migrate past the detection area. Once all 10 samples have been loaded into each capillary, continuous electrophoresis and scan analysis of the detection area occurs (block 55). This electrophoresis and analysis requires 20 to 30 minutes. In this time all the samples migrate past the detection area. As the samples migrate past the detection area, detectable targets within the sample may be detected. The electrophoresis and analysis produces detection signals. The detection signals are gathered as data that is subsequently processed (block 57). In the data processing, the base line detection noise is subtracted from the spectral separation to eliminate signal background. This allows some normalization of the detection data and elimination of false signals. The data may then be analyzed to find presence of target compounds.

Once detection data are collected and processed, allele calls are made (block 61) based on detection of target compounds by wavelength emission and/or target migration rate. The target compound may be classified as indicative of an allele genotype.

Analysis of single nucleotide polymorphism allows genotype characterization based on single base differences at particular loci (block 63). As already noted, single nucleotide polymorphism provides high content genotyping information and may be an indicator of phenotypic disease states.

The capillary electrophoresis analytical methods shown in flow charts in FIGS. 1 and 2 are useful for increasing the throughput of the analysis of any of the number of small compounds, as long as the target compounds are of a known discrete size range such that the expected rate of electrophoretic migration may be determined. Numerous protein and nucleic acid analytical procedures may be aided by this higher throughput method. The methods are especially useful for aiding in the analysis of single nucleotide polymorphisms.

A "polymorphism" is a variant of a DNA sequence found in some individuals within a population. Polymorphisms may be characterized as "allelic", that is, one of at least two locus variants. Single nucleotide polymorphisms indicate that the difference between the two variant alleles is a change in a single nucleotide base at a specific genomic location. If only two variants are present within the population, the single nucleotide polymorphism is characterized as diallelic.

For organisms which have two copies of the genome chromosomes (diploid organisms) three genotypes are possible. Any individual can be homozygous for one allele (both chromosomes have the same base at the locus of interest), may be homozygous for the alternate variant allele (both chromosomes have the variant type base at the locus of interest), or may be heterozygous (one chromosome has each type allele). Single nucleotide polymorphisms which are diallelic are adaptable to a binary type (+/−) scoring that simplifies data gathering and analysis. If a single nucleotide primer extension (SNuPE) reaction is used to analyze the polymorphism, the reaction products are highly predictable and uniform allowing for more controlled predictability in determining electrophoretic mobility.

FIG. 3 illustrates the steps of a single nucleotide primer extension (SNuPE) reaction. Step one of the reaction requires providing template DNA composed of a first DNA strand 105 and the second DNA strand 107. In a second step the two strands of template DNA 105, 107 are separated into single strands. One of the single strands, strand 105, contains the polymorphisms at single nucleotide loci to be assayed.

In step 3, three primers are introduced. The three primers 101, 102, 103 are complementary to specific regions on template DNA 105. The length of primers 101, 102, 103 each differ from each other by at least three bases. For example if primer 101 is 15 bases long, primer 102 would be 18 bases long and primer 103 would be 21 bases long.

Added to the mixture of template DNA with annealed primer in step 4 are one or more terminators with detectable labels. The labeled terminators anneal immediately downstream of the 3'-end of the primers to a complementary base on the template strand. As shown in FIG. 3, the two terminators used are labeled dideoxyinucleotides, namely dideoxyadenosine triphosphate (ddATP) 131 and dideoxyguanosine triphosphate (ddGTP) 133. ddATP 131 is labeled with first optically detectable dye 111 and ddGTP is labeled with second optically detectable dye 113. Each optically detectable dye has a characteristic absorption and emission wavelength. This allows the optically detectable dye to be selectively excited and detected. The nucleotides will attach to the complementary base on the template DNA. For example thymine base 135 on template DNA 105 is complementary to adenine. In a similar manner, the cytosine base 137 is complementary to guanine. In step 4, the terminators are added along with an inducing agent, such as a DNA polymerase. The inducing agent bonds the terminator to the 3'-end of the primer. As shown in step 4, the single nucleotide polymorphism at the single base immediately upstream of the 3'-end of each primer is a diallelic variant. The polymorphic loci has either thymidine or cytosine at the location on the template strand 105 immediately opposite the location one base upstream from the 3'-end of the primer.

In step 5, the single nucleotide primer extension products are isolated. The isolated products 141, 142, 143 each have been extended by one base. The one base added to the 3'-end of each primer is a base complementary to the base opposite the 3'-end on the template DNA strand 105. The one base added on to each primer is a terminator base labeled with an optically detectable labeling agent. These products are then analyzed to determine which terminator has been added to each primer.

In the method shown in FIG. 3, an assay is enabled in which allele calls for specific loci on a template DNA may be determined for a plurality of different loci on that template DNA strand. The use of different primers allows for the simultaneous analysis of different loci on the template strand, and the use of different optically labeled terminators allows the diallelic variation at each locus to also be simultaneously analyzed. Single nucleotide primer extension products 141, 142, 143 are each extended by a single terminator base complementary to the single nucleotide on the template DNA immediately opposite the 3'-end of any primer. The added terminator is labeled with an optically detectable label to allow the product to be specifically detected. To avoid optical interference from excess dideoxynucleotide terminators as well as optical interference from the template DNA, both excess labeled dideoxynucleotides as well as the template DNA are removed from the sample reaction before the single nucleotide primer extension reaction products are analyzed.

The single nucleotide primer extension reaction is one method of preparing samples which generates small molecule samples of a known size and migration rate. Numerous other sample preparation methods are also available. As noted, PCR uses matched sets of primers to amplify DNA sequences. The resultant reaction product may be of a discrete size range. For example, primers can be designed that anneal to non-variable (conserved) sequences that flank a variable region. In the case of short tandem repeats (STR), the variable region is a nucleotide sequence of 8 bases or less that repeats sequentially. The number of repeats is variable. The amplification of STR loci produces products in a known discrete range of sizes.

Compounds of a discrete size range are also produced by high performance liquid chromatography (HPLC) separation. HPLC separation requires a separation column into which the sample is introduced. This separation column contains a packed particulate material (stationary phase). Flowing through this packed material is a liquid (mobile phase). Target compounds move as a zone in the column as the liquid flows. Thus the target compound will elute from the column at a specific time. Thus if eluted fractions of the liquid flowing through the column are collected, the sample will be concentrated in a specific fraction. Compounds isolated by HPLC can be further analyzed by capillary electrophoresis. The uniformity of HPLC isolated compounds produces a uniform electrophoretic rate. These isolated compounds, whether protein, nucleic acid, or other compounds are adaptable for analysis using the multiple time-spaced injection methods of the present invention. Numerous other methods to produce small compounds are known. These include alternative DNA amplification techniques used for SNP analysis.

FIG. 4 illustrates the data from a single primer used in a SNuPE reaction to investigate a single locus. The data in FIG. 4 is gathered from analysis of a sample generated by using a single primer extended with one of two labeled terminator nucleotides. Peaks 151*a*, 151*b*, 151*c* are from the third, second, and first injection into a capillary column, respectively. As the graph shows, the primer extension products are detectably separated. Location of the signal is dependent upon the characteristic migration rate of the oligonucleotide labeled with a specific optical label. The optical label has a characteristic excitation and emission wavelength. The presence of a single peak in each injection interval indicates that the template strands of DNA from a diploid organism contain the same allele type on both chromosomes. As noted earlier, this would be considered a homozygote. The emission wavelength is dependent upon the dye attached to the specific terminator. The specific terminator for the top row of injections shown is indicative of the single nucleotide primer extension product incorporating the ddATP terminator. This product is indicative of the wild type allele.

In the central data reading of FIG. 4 is the data gathered from a second single nucleotide primer extension reaction. As was the case in the top graph, the central graph shows a first, second and third injections with a selected interval between injections. Peaks 153*a*, 153*b*, 153*c* indicate detection at a distinct wavelength. This indicates that a ddGTP terminator was incorporated into the single nucleotide primer extension products. The injections are spaced such that the samples are detectably separated when the target compounds reach a detection window.

The bottom graph represents the data from a heterozygotic individual. The peaks on the graph show that of the single nucleotide primer extension products some of the reaction products incorporated the ddATP terminator and some of the products incorporated the ddGTP terminator. Thus, for each of the three repeated sample injections, each injection from a heterozygotic individual has two characteristic peaks. Each peak represents a readout from an analytical system that has detected a specific emission wavelength intensity represented by each peak. Peaks 151*d*, 151*e*, 151*f* represent the incorporation of the ddATP terminator with associated optical label. Peaks 153*d*, 153*e*, 153*f* represent single nucleotide primer extension products incorporating the ddGTP terminator with associated optical label. As was the case with the top and central data readouts, the three injections shown in the bottom graph are spaced sufficiently far apart that by the time the detectable targets reach the detector, there is sufficient separation both between samples as well as between target compounds within the samples to distinguish both individual samples and component target compounds.

FIG. 5 shows the data graph from optical detection of separated compounds in a single capillary. In the capillary, ten injections have been made at equal time spaced intervals. After the final injection, continuous capillary electrophoresis procedure caused target compound migration and simultaneous scanning of a detection window enabled a continuous detection of the targets in the migrating samples (as described in FIGS. 1 and 2). FIG. 5 shows a repeating pattern of three peaks. Peaks 161*a*–161*j* measure the intensity of emission of one wavelength indicating a first target compound. Peaks 163*a*–163*j* and peaks 165*a*–165*j* measure two other emission wavelength intensities indicating detection of two additional target compounds. Each set of peaks 1 through 10 indicates the data detected by the system detector from a single sample injection. Peaks 161*a*–161*j* and peaks 165*a*–165*j* are peaks representative of two optically detectable targets included within each of ten samples. The consistency between the data peaks from separate injections is indicative of the high reproducibility of the present multi-injection analytical system.

Peaks 163*a*–163*j* are indicative of a quality metric standard included with each sample. A quality metric standard has a characteristic migration rate, characteristic emission wavelength, and/or a characteristic peak size. This enables the quality metric standard to produce characteristic known detection data. The quality metric standard can then be used to normalize detection data or assess the quality of the run, the reaction, or the detection event.

The quality metric standard may take different forms. For example if the separation run is separating compounds based on compound size, the quality metric standard may be a specific sized fragment. Additionally the amount of the quality metric standard included in each sample may be tightly controlled. The control of the amount of standard results in highly reproducible quality metric data peaks. The size of the data peak from the quality metric standard may then be compared to other peaks in the run to determine the amount of sample analyzed. If the quality metric standard has a specific fluorescent wavelength, the specific fluorescent wavelength may be used to compare to other measured wavelengths within the sample run. The intensity measured of the quality metric standard signal may be used to ensure proper functioning of the system by indicating defects in laser power, detector function, and other possible system problems. Broadening of the peak profile may be used to determine the integrity of the capillary and/or quality of the separation media. Peak broadening of the standard may also be indicative of problems with the injection.

The use of a quality metric reference standard as an optically detectable co-migrating compound having known physical properties has been described in U.S. patent application Ser. No. 09/036,676 hereby expressly incorporated by reference herein. The quality metric standard allows a quality measurement of resolution of the sample peaks, allows the computation of signal-to-noise ratio, and allows determination of linearity of compound separation. In a sample run, the quality metric standard may be used for any or all of the above stated functions.

It is also possible to design the quality metric standard to measure the quality of the sample preparation procedures. For example in a PCR-based DNA amplification system, the use of a known set of primers to produce a standard of known length may be used as a check for the reagents used in the PCR amplification procedure.

The data set shown in FIG. 6 shows another graph of intensity peaks from optically detected targets. Like the graph of FIG. 5, the data of FIG. 6D represents detection readings from ten injections made at time spaced intervals into a capillary in an electrophoresis system. The FIGS. of 6A–6C represent the signals detected at different wavelengths. The peaks 175*a*–175*j* in FIG. 6A represent the data signal at one characteristic wavelength. The peaks in FIGS. 6B and 6C represent the signals from a second and third distinct wavelength. The FIGS. 6A through 6C are combined in FIG. 6D into a single graph. As seen in FIG. 6D, peaks 171*a*–171*j* (peaks seen in FIG. 6C) and peaks 173*a*–173*j* (peaks seen in FIG. 6B) are occupying the same location at the time of detection. Despite the fact that the two compounds represented by these detection events migrate at equal rates, the compounds are distinguishable due to different target emission wavelengths. If the compound represented by the detection event shown by peak 171*a–j* or 173*a–j* is a quality metric standard, the overlay of the two peaks allows for ready comparison of the migration rates expected from a target compound as compared to the migration rate of the quality metric standard.

There are clear advantages of increasing throughput in analytical systems. By using a single capillary electrophoresis system, a single sample may be analyzed in a given separation procedure. By using an array of capillaries, the number of samples analyzed is increased by the number of capillaries in the array of capillaries. Presently some capillary array systems are adapted for use with microplates. These analytical systems have 96 capillaries in an array, increasing throughput 96-fold.

By using different optically detectable dyes, throughput may be further increased. Optical detectors may detect several different wavelengths emitted by several different energy transfer or other dyes. If two dyes are utilized for labeling a pair of allelic variants at a genetic locus, the use of eight dyes allows the simultaneous wavelength based distinction in a single sample of three pairs of loci leaving two dyes for use with the quality metric standards or injection markers.

The use of multiple primers or primer sets in PCR type sample preparation procedures allows a further increase in throughput. Dyes are distinguishable by the detector that records the wavelength of the emission from the capillary.

The size of the detectable target would be detectable by determination of the migration rate (i.e. the time required before the target reaches a detector). Throughput may be increased with each additional primer or primer set used enabling an additional locus to be assayed in the same single sample preparation. Thus if two primers or primer sets are used, the loci analysis throughput doubles.

The use of temporally spaced injections allows one further method to increase throughput. In the methods shown in FIGS. 1 and 2 producing the data shown in FIGS. 5 and 6, ten time spaced sample injections into a capillary allow the capillary analytical procedure to accommodate ten times the sample throughput. By using time spaced injections into capillary arrays to analyze samples prepared with multiple primer sets and multiple optically detectable dyes, the original throughput of a single sample in a two hour period may be increased to 5,760 samples processed in the equivalent amount of time. [96 capillaries×10 sample injections per capillary×3 target size variants×2 color alternative variants] By further increasing the amount of primers used in sample preparation to add additional target size variation or by increasing the sample processing by pooling samples would allow for still further increase in throughput.

Although the benefits to increasing throughput are manifest, the present methods have not been adopted due to design limitations in capillary array analytical systems. To effect the present method requires an injector for the capillary array electrophoresis system that can make multiple injections into the same separation medium in rapid succession. The present injection systems have not been designed for multiple injections followed by analysis of the injected compounds. Such a system requires at least some modification to present systems and additional steps in separation procedures to effect the present method.

Some injection systems rely on robotic transfer of samples from a multiwell sample plate to injection ports. The samples are transferred by a robotic system in which multiple samples are transferred by a robotic arm. The robotic arm periodically must register location to ensure that the samples are properly transferred to the corresponding injection ports. After 96 samples have been transferred to the injection ports, the samples may be injected into the capillaries. Currently available systems using robotic transfer to a 96-capillary array requires at least 8 and up to 20 minutes to transfer the 96 samples into the injection ports. Given the relatively long time for transfer of samples, the injection spaced over time described in the present invention is not practicable in such systems.

A second type of capillary array analytical system uses an eight-capillary array with the wells of a microplate. Each sample is analyzed after which the capillary array is emptied of matrix, washed, dried, and refilled with matrix. A subsequent sample is then loaded onto the column and analyzed. Using this system, 96 samples may be analyzed in twenty-four hours. It is also believed that this system would make the temporally spaced injection of samples more difficult while maintaining the integrity of the analytical procedure.

The MegaBACE 96-capillary electrophoresis system produced by Molecular Dynamics of Sunnyvale, Calif., a subsidiary of Amersham Pharmacia Biotech provides a system which has been adapted to temporally spaced injection as a method to increase throughput. In this system the 96-well sample plate is contained on a cathode stage. The stage is moved into a position such that the capillaries in the array are in contact with the samples contained in the sample wells of a microplate. A small amount of the sample is injected into each capillary by means of an electrical pulse. The capillaries are then moved into a reservoir tank and the electrophoretic separation of the samples within each capillary is effected. Currently in the MegaBACE system, samples may be injected every two minutes. The timing of the injection is presently limited by the system restricting the ability to open the cathode door and unload a sample plate. It is possible to modify this system such that more rapid injections are possible. Presently up to ten injections spaced in two minute intervals may be made. Following the ten injections, continuous electrophoresis and scanning allows further separation and detection of target compounds. It is possible to modify the MegaBACE system such that continuous electrophoresis during sample injection and detection procedures is enabled. In such a system, a mechanical means would be used to continuously bring new sample plates onto the cathode stage.

The schematic for an apparatus adapted for temporally spaced injection is shown in FIG. 7. In FIG. 7 blue laser 201 directs blue laser light 210 through filter 205 and shutter 209 to impinge upon steering mirror 211. Steering mirror 211 directs blue laser light through beam combining mirror 213. Simultaneously, green laser 203 produces green laser light 212 which is directed through filter 207 and shutter 209 to impinge upon beam combining mirror 213. In this way, blue laser light 210 and green laser light 212 are combined into excitation beam 214. Excitation beam 214 is directed by steering mirrors 215, 240, and 242 and passes through beamsplitter 217. Beamsplitter 217 is selected to have one side that would allow passage of a beam of the wavelength of excitation beam 214. Beam 214 is then directed by steering mirror 219, through beamsplitter 221, and onto scan head 223. Scan head 223 produces a two dimensional scan of light across the detection windows 261 in detection window block 260.

Some light from excitation beam 214 is reflected from window block 260 back onto scan head 223. Scan head 223 directs the light back onto a reverse side of beamsplitter 221. This side of beamsplitter 221 is selected to allow passage of light of the wavelength of excitation beam 214. The reflected excitation beam 216 then impinges upon steering mirror 219 that directs the reflected excitation beam 216 onto beamsplitter 217. The side of beamsplitter 217 onto which reflected excitation beam 216 is directed reflects light of the wavelength of reflected excitation beam 216 through filter 225 and onto photodiode 227. Photodiode 227 continuously monitors the beam power of reflected excitation beam 216. This provides some indication of proper laser power output, system energy fluctuation, and proper alignment of system components.

Light of the wavelength of excitation beam 214 will also excite fluorescence from the compounds passing through detection window 261. The excitation light 218 is of a different wavelength from the wavelength of the excitation beam 214. Excitation light 218 is directed by scan head 223 onto beamsplitter 221. Beamsplitter 221 is selected such that the side onto which emission light 218 impinges will be reflected by beamsplitter 221 through filter 244 and onto lens 229. Lens 229 focuses emission light 218 through pinhole filter 231 and onto lens 233. After passing through lens 233, emission light 218 impinges upon beamsplitter 235. Beamsplitter 235 is selected to allow light with wavelength above a selected wavelength to transmit through while light with a wavelength below the selected wavelength is reflected. In this way, beam 218 is divided into reflected beam 232 and transmitted beam 236. Reflected beam 232 passes through filter 237 and onto first detector 241. Transmitted beam 236 passes through beamsplitter 235, through filter 243 and onto second photodetector 245.

The signal from photodetector 241 is transmitted as a digital signal by electronic link 247 into an electronic memory and data processor 251. In a similar manner, the signal collected by second photodetector 245 is transmitted by electronic link 249 and is also collected by electronic memory 251. This data can be saved in the electronic memory and simultaneously viewed on a view screen as graphic data 250.

This system is designed to excite fluorophores using defined excitation and emission wavelengths. Such fluorophores include energy transfer dyes. Such fluorophores migrate through the detection area 261, the migration effected by a capillary electrophoresis system.

The present examples have described systems using optical detectors to detect target compounds labeled with optically detectable fluorescent labels. Alternative detection systems could also be used. For example ultraviolet detectors, infrared mass spectrometry or conductivity detectors may be used to detect target compounds. In addition radiometric, Raman-based, or refractive index detectors may be used as detectors in capillary electrophoresis systems. If a radiometric detector is used, the target compound is labeled with a radioactive marker.

The capillary electrophoresis system is composed of a capillary 273 contained in an array of capillaries. A set of 16 such capillaries is held in a defined relation on a cathode bar 271. The 16 capillaries, held by cathode bar 271, each are positioned to fit into a single well in a 96-well sample plate. Samples may be injected into the capillary array by moving cathode stage 280 such that sample plate 279 is in a position such that the capillaries on cathode bar 271 are inserted into the wells on sample plate 279. A pulse of electrical current through the capillaries will then draw by electrophoretic sample migration a small amount of sample into each of the capillaries in the array of capillaries. Cathode bar 271 is then repositioned relative to cathode stage 280 to bring the capillary array into the wells first of the 24-well cathode water tank 277 and then into the wells of the 96-well cathode plate 275. Cathode plate 275 is in electrical communication with power source 285 by an electronic link 287. With the capillaries in 96-well cathode plate 275, the injected samples migrate through the capillary if the distal end of the capillary is in electrical communication with an anode.

Cathode stage 280 may be moved to relocate the capillaries in cathode bar 271 from 96-well cathode plate 275 to a sample plate 279. As indicated in the flow chart in FIG. 1, following injection of samples the cathode stage 280 may be moved to relocate the capillaries in cathode bar 271 into 24-well cathode water tank 277. The tips of the capillaries may then be rinsed in cathode water tank 277 before the stage 280 repositions the capillaries in cathode bar 271 into 96-well cathode plate 275.

Although only a single cathode bar is shown, the electrophoresis system will include six such bars. The 6 bars hold 96 capillaries enabling all 96 wells in a sample plate may be simultaneously injected into corresponding capillaries. Detection window block 260 and the scan system also are adapted to accommodate capillaries from six cathode bars to enable an optical scanning system in which 96 capillaries are simultaneously scanned.

The capillaries extend from cathode bar 271 through detection window block 260 and terminate in anode plug 297. Anode plug 297 extends through anode cover hole 303 on anode cover 301 into anode reservoir 305 on anode reservoir holder 295. Anode reservoir 295 is linked to a power supply 285 by electronic link 293. Thus when one end of the capillary 271 is inserted into 96-well cathode plate 275 and the distal end of capillary 271 is inserted into anode reservoir 295, power from power supply 285 introducing electric current through the media in the capillary effects electrophoretic separation. Power supply 285 can be programmed to supply a selected current through the system.

Anode plug 297 may also be inserted into media reservoir 307. Media reservoir 307 may be pressurized by high pressure nitrogen line 299. The pressurized media may then be driven into capillary 273 allowing for media to fill the capillaries in the capillary array. Preferably the capillaries are washed before exchange of media. Coated capillaries are preferred and may be reused for numerous separation runs depending upon the stability of the capillary coating.

Use of an alternative, low viscosity media (such as free solution media) would eliminate the need for high pressure nitrogen for media exchange. Instead media could simply be pumped into the capillary.

The use of timer 281 allows for time spaced injection of samples into the capillary array. Timer 281 is linked by electronic link 289 to the cathode stage 280. At programmed intervals, the timer 281 sends a signal to cathode stage 280 to move the stage such that the capillaries are brought out of electrical communication from the 96-well cathode plate 275 and into communication with a new sample plate 279. Cathode bar 271 is linked by electronic link 289 to timer 281. Cathode bar 271 then is instructed by timer 281 to introduce a brief pulse through the capillaries to introduce a sample from sample plate 279 into each capillary in the array of capillaries. Timer 281 is also linked to power supply 285. Thus, moving the capillaries from the cathode plate to a sample plate effects the cycle of temporally spaced injections. A pulse of electrical current introduces a determined amount of sample into the capillary array. The capillary array then moves back into the cathode plate to enable electrophoretic separation of the samples within the plate for a given interval. This procedure may be effected continuously with minimal interruption of current flow. Alternatively, the timer 281 may instruct power supply 285 to pulse the power flow through the cathode and anode during sample injection.

Presently the limitation in the MegaBACE system is that the system design requiring the doors on an exterior shell to be opened only after specific system components are in place. This limits the injection interval to once every 2 minutes. However it is envisioned that the interval between injections may be reduced from a two-minute interval to an interval as short as 20 seconds, enabling a further 12-fold increase in throughput. This is enabled by alteration to the system to more readily feed additional sample plates. The only limiting factor is the ability to detectably distinguish injected samples. This is the function of the range of electrophoretic mobility of the target compound analyzed.

The system may be further modified to allow for increased throughput in the system. A system of automatically moving new plates to the sample plate location as shown in FIG. 8 would be needed for the rapid injection of samples. Such a system would use a mechanical grip 355 moved by a robotic arm 353 to place samples upon cathode stage 280. Such a conveyor would transfer prepared sample plates 279 from a magazine 351 onto cathode stage 280. It is also possible to use a conveyor to move sample plates to this location. By locating the magazine to feed internally into the capillary array electrophoresis system, the speed of the procedure may be enhanced.

The method and apparatus of the present invention represent a way to increase the throughput analysis of small compounds. The increase in throughput should prove especially useful for single nucleotide polymorphism genotyping utilizing capillary electrophoresis instruments, especially instruments with highly parallel capillary systems.

What is claimed is:

1. A method of analysis of molecules in a capillary dimension channel(s) filled with a separation media, the method using electrophoretic separation to separate small compounds, the method comprising:
   a) injecting a sample into a injection end of said capillary dimension channel, said sample including at least one small molecule and at least one quality metric standard compound;
   b) introducing an electric field through the capillary dimension channel for a selected period of time, whereby said electric field causes compounds in said sample to migrate away from said injection end;
   c) repeating steps a and b at least one time; and
   d) detecting at a detection location said at least one small molecule and at least one quality metric standard compound; wherein said detection location is separated from said injection end by a length of the capillary dimension channel;
   wherein said selected period of time is sufficient to allow the compounds in each sample to be detectably separated at the detection location;
   wherein every sample injected into the capillary dimension channel is continuously detected.

2. The method of claim 1, wherein the step of injecting said sample includes injecting a sample containing nucleic acids.

3. The method of claim 1, wherein the step of injecting said sample includes injecting a sample containing a DNA fragment.

4. The method of claim 1, wherein the step of injecting said sample including at least one quality metric standard includes injecting a sample including a nucleic acid quality metric standard.

5. The method of claim 1, wherein the method is effected in a plurality of capillary dimension channels in an array of capillary dimension channels.

6. The method of claim 1, wherein the step of detecting is effected by illuminating the detection location and detecting a detection signal produced by the small molecule and the quality metric standard compound, said detection signal excited by illuminating the detection location.

7. The method of claim 6, wherein the step of illuminating the detection location includes illuminating using laser illumination.

* * * * *